(12) United States Patent
Warburton

(10) Patent No.: US 6,319,375 B1
(45) Date of Patent: Nov. 20, 2001

(54) APPARATUS FOR IDENTIFYING A GAS

(75) Inventor: P. Richard Warburton, Moon Township, PA (US)

(73) Assignee: Industrial Sceintific Corporation, Oakdale, PA (US)

( * ) Notice: Subject to any disclaimer, the term of this patent is extended or adjusted under 35 U.S.C. 154(b) by 0 days.

(21) Appl. No.: 09/671,696

(22) Filed: Sep. 28, 2000

Related U.S. Application Data

(62) Division of application No. 09/310,330, filed on May 12, 1999, now Pat. No. 6,165,347.

(51) Int. Cl.[7] .................. G01N 27/404; G01N 27/16
(52) U.S. Cl. .................. 204/409; 204/400; 204/431; 205/793; 436/152; 422/97
(58) Field of Search .................. 205/775, 781, 205/782.5, 779.5, 786.5, 787, 793, 783; 204/400, 409, 431, 432, 415; 436/116, 118, 120, 122, 124, 133, 140, 141, 142, 143, 144, 148, 152, 159; 73/23.31; 422/94–99

(56) References Cited

U.S. PATENT DOCUMENTS

| | | | |
|---|---|---|---|
| 4,279,727 | * 7/1981 | Scheubeck et al. | 204/409 |
| 4,829,809 | * 5/1989 | Tantram et al. | 73/23.36 |
| 4,861,557 | * 8/1989 | McNally | 422/97 |
| 5,591,898 | * 1/1997 | Mayer | 73/38 |
| 5,741,413 | * 4/1998 | Capetanopoulos | 205/783 |
| 5,902,467 | * 5/1999 | Wang et al. | 204/415 |
| 6,096,186 | * 8/2000 | Warburton | 73/1.06 |

OTHER PUBLICATIONS

Podkowka et al "Comparative Evaluation of Diffusion Coefficients for Gases and Vapors of Organic Substances through Polyethylene Membranes Determined by Absorption and Desorption Upstream Time Lag Method", J. App. Polymer Sci. 27, pp. 1471–1478, month N/A, 1982.*

Partingon, An Advanced Treatise on Physical Chemistry: The Properties of Gases, pp. 900–913, month N/A 1950.*

* cited by examiner

Primary Examiner—Robert J. Warden, Sr.
Assistant Examiner—Kaj K. Olsen
(74) Attorney, Agent, or Firm—Dennison, Scheiner, Schultz & Wakeman

(57) ABSTRACT

An apparatus for identifying an unknown reactive gas in a carrier gas, utilizing a sensor with a diffusion limited inlet. The apparatus includes a manifold of predetermined volume having an inlet and outlet, an inlet valve in the manifold inlet, an outlet valve in the manifold outlet, a gas detector in communication with the manifold, a diffusion barrier disposed between the manifold and the gas detector for limiting diffusion of gas from the manifold into the gas detector, means for opening and closing the inlet and outlet valves, means for detecting an output signal from the gas detector, means for determining a coefficient of diffusion for the reactive gas from the output signal, and means for identifying and quantifying the reactive gas from the determined coefficient of diffusion.

13 Claims, 5 Drawing Sheets

APPARATUS FOR IDENTIFYING A GAS

This application is a division of U.S. application Ser. No. 09/310,330 filed May 12, 1999, now U.S. Pat. No. 6,165,347.

BACKGROUND OF THE INVENTION

1. Field of the Invention

The invention relates to a method and apparatus for identifying a component of gas mixture.

2. Description of Related Art

Potentially dangerous gas mixtures may be found in many workplace environments, the dangers including the risk of fire or explosion from combustible gases, oxygen enrichment or deficiency and exposure to toxic gases. These dangers are well known and gas detection instruments are available to detect a wide range of gases. These instruments typically contain one or more gas sensors, which give a proportional electrical response dependent upon the concentration of the gas to be detected. If the concentration exceeds allowed concentration limits, then the instrument will provide an alarm to warn nearby personnel, or it may activate other remedial action, such as increasing, the ventilation. Gas detection instruments for safety applications are broadly divided into two groups, portable instruments, which are designed to be hand held or worn by the user and provide personal monitoring, and fixed instruments, typically wall mounted, which provide area monitoring.

Combustible gases are often characterized by their lower explosive limit, (LEL), which is the minimum concentration of that particular gas in air, which can support combustion. If the concentration is below the LEL, then the gas will not burn without the continued support of an external ignition source. If the concentration of the gas is greater than the LEL, then once ignited, the combustible gas-air mixture will burn, without the need for an external heat source. Indeed, many combustible gas-air mixtures will explode if ignited at concentrations greater than the LEL. At very high concentrations of the combustible gas, there may be insufficient oxygen to support the combustion, and the combustible gas-air mixture will no longer burn. This upper concentration limit for flammability is known as the upper explosive limit (UEL). The upper and lower explosive limits depend on the gas to be detected, as may be seen from the following data, taken from the CRC Handbook of Chemistry and Physics, 68$^{th}$ Edition, 1987–1988, CRC Press, Boca Raton, Fla. Limits of Flammability of Gases in Air

| Gas | | LEL (% vol.) | UEL (% vol.) |
| --- | --- | --- | --- |
| Acetylene | HCCH | 2.50 | 80.00 |
| Ammonia | NH3 | 15.5 | 27.0 |
| Benzene | $C_6H_6$ | 1.40 | 7.10 |
| Hydrogen | $H_2$ | 4.00 | 74.24 |
| Methane | $CH_4$ | 5.00 | 15.00 |
| Pentane | $C_5H_{12}$ | 1.40 | 7.80 |
| Xylene | $C_6H_4(CH_3)_2$ | 1.00 | 6.00 |

There are three main types of sensors used to detect combustible gases. For general leak detection, metal oxide, especially tin oxide sensors are used. The electrical conductivity of the metal oxide changes when exposed to the combustible gas at high temperatures. These sensors are rarely used for safety monitoring, since they commonly lack the precision necessary for this application.

Infrared sensors typically measure the absorption of the gas at 2940 cm$^{-1}$ (~3.4 $\mu$m), which corresponds to the carbon-hydrogen (C—H) bond stretching frequency. The absorption of the infrared light depends on the number of C-H bonds stretching in the molecule. One of the limitations of infrared detectors is that molecules such as carbon monoxide (CO) and hydrogen ($H_2$) do not have an absorbance at or near 3.4 $\mu$m bond, since they do not have any C—H bonds. Even molecules such as acetylene (HCCH) and benzene ($C_6H_6$) which both have C-H bonds often have low sensitivity at 3.4 $\mu$m since the triple bond in acetylene and the aromatic ring in benzene shift the absorbance of the C—H stretch to higher frequency. These effects of molecular substitution on the C—H bond vibration frequency are well known, and can be found in standard texts such as D. H. Williams, I. Fleming, "Spectroscopic methods in Organic Chemistry", third Edition, McGraw-Hill book Company, Ltd., London, 1980.

The other major type of sensor for combustible gas is the catalytic bead sensor, which measures heat of combustion. The detector bead of a catalytic bead sensor comprises a small platinum coil encased in a ceramic bead containing precious metal catalysts. The combustible gas enters the sensor and travels to the catalytic bead by natural diffusion. The gas is combusted at the bead surface, aided by the catalysts and the resulting release of heat raises the temperature of the bead. This rise in temperature results in an increase in resistance of the platinum coil, which is normally detected using a Wheatstone bridge. Within the sensor, there is usually a second bead, the reference or compensator bead, which is constructed similarly to the detector bead, without the catalyst. The compensator bead comprises one of the other arms of the Wheatstone bridge, and it is used to cancel out any other non-combustion related responses of the beads, such as changes in ambient humidity or thermal conductivity of the gas. The response of the catalytic bead depends primarily on the heat of combustion of the gas and the rate at which the gas can diffuse to the detector bead.

It is common practice to express the concentration of combustible gases as a percentage of the LEL, and thus 2.5% by volume of methane is 50% LEL. The response of catalytic bead sensors is approximately linear over their useful range (0 to 100% LEL), and setting the empirically determined proportionality constant between the output response and the concentration is called calibration. However, the sensitivity to gas varies with the type of gas. Compared to a relative response to 50% LEL of methane of 1.0, the response to 50% LEL pentane is only about 0.5. A more thorough discussion of catalytic bead sensors may be found in the review by J. G. Firth, "Measurement of Flammable Gases and Vapors" in C. F. Cullis, J. G. Firth (Eds.), "Detection and Measurement of Hazardous Gases", Heinemann, London, 1981.

Many of the commonly encountered toxic gases are detected using amperometric electrochemical gas sensors. A typical electrochemical sensor is usually constructed with two or more electrodes in contact with an electrolyte. The electrode is usually separated from the outside environment by a gas porous membrane, and other diffusion barriers. The gas to be detected enters the sensor and passes through the membrane to the working electrode, where is it either oxidized or reduced; alternatively, the rate of oxidation or reduction of the electrode or another species in electrolyte may be limited by the availability of the toxic gas. The resulting electrical current is proportional to the rate at which the gas is being consumed by the electrode. The output current is therefore usually linearly proportional to the gas concentration, since the response is limited by the rate at which the gas to be detected can diffuse into the sensor.

The nature of the response of the sensor to a toxic gas depends on both the design of the sensor and the nature of the gas. Some gases such as carbon monoxide (CO) and hydrogen ($H_2$) are oxidized at the electrode, whereas other gases such as chlorine and nitrogen dioxide are usually reduced at the sensor electrode. While the oxidation of carbon monoxide to carbon dioxide ($CO_2$) is a two-electron process, the oxidation of hydrogen sulfide ($H_2S$) to sulfuric acid ($H_2SO_4$) is an eight-electron process. Thus, a diffusion limited sensor which responds to both hydrogen sulfide and carbon monoxide will give a stronger response to the hydrogen sulfide, for a given concentration of gas.

The above examples of sensor technology are intended to illustrate that the signal obtained for a combustible or toxic gas depends on both the sensor technology employed, and on the properties of the individual gases. This fact poses a quandary for personnel who risk being exposed to a variety of different gases. If they use a broad band sensor, i.e. a sensor that is sensitive to a wide variety of gas types, then there is the Ahrisk that the alarm levels will not be appropriate for any given gas. However, if they instead decide to use sensors selective for a particular gas, then there is the risk that if an unanticipated hazardous gas is present, then it may not be detected at all. In addition, they may have to use instruments which contain many sensors or they may have to carry several instruments, which may be both expensive and cumbersome.

It is now common practice to use a broad band sensor for combustible gases, such as a sensor based on infrared or catalytic bead technology, and to set the alarm levels to match the gas with the least sensitive response. If there is likely to be either methane or pentane in a particular environment, then a catalytic sensor based instrument will usually be calibrated with pentane, since pentane has the lower sensitivity. However, this approach can result in false alarms since a safe concentration of methane will set the instrument into alarm. With a broad band sensor, such as the catalytic bead sensor, it is not currently possible to distinguish whether a response is coming from methane or pentane.

In contrast, toxic gases are usually detected with sensors specific to a particular gas. This difference between the combustible gases and the toxic gases is in part due to the wide variation in risk associated with a toxic gas. For example, carbon dioxide has an OSHA eight-hour permissible exposure limit (PEL) of 5000 ppm, carbon monoxide has a PEL of 50 ppm, sulfur dioxide has a PEL of 5 ppm and chlorine dioxide has a PEL of 0.1 ppm. Another reason for this difference is that it is often easier to fabricate an electrochemical sensor to be selective to a particular toxic gas than to fabricate a catalytic bead sensor to be selective to a particular combustible gas. Some attempts have been made to produce broad band electrochemical gas sensors, but they also suffer from the drawback of deciding where to set the alarm levels. For example, a sensor which gives a response to both sulfur dioxide and carbon monoxide, corresponding to 10 ppm, is five times below the OSHA PEL for carbon monoxide but twice the OSHA PEL for sulfur dioxide, even though both gases are oxidized by two electrons.

Clearly, a method would be desirable that enables a gas detection instrument to identify the gas, and then select the appropriate alarm threshold levels to be used.

Several methods have been developed to identify the components of a potentially hazardous atmosphere. Detector tubes kits are available, in which a series of calorimetric tubes are used, initially identifying the unknown gas by broad chemical classification (e.g. acidic, halogenated or reducing gas), followed by successive iterations until the gas is identified. However, this manual approach is time consuming, cumbersome, and provides the analysis only at a single moment in time ("Drager-Tube Handbook," $8^{th}$ Edition, National Draeger Inc, Pittsburgh, Pa.).

In the past, gases were identified by collecting a sample, either on an absorbent, such as activated charcoal, or in a clean gas chamber, followed by laboratory analysis. This method is time consuming and since the analysis has to be performed elsewhere, there is often a considerable delay from the time the sample is taken to the time when the identity of the gas is determined.

Laboratory based methods for gas identification usually involve large, expensive and immobile equipment, such as mass spectrometers, gas chromatographs and infrared spectrometers. Considerable effort has been made to adapt these laboratory instruments for use in the field, and several manufacturers do offer portable gas chromatographs (for example HNU Systems, Newton Mass. 02461 and Viking Instruments Corporation, Chantilly, Va. 20151). Mass spectrometers offer high sensitivity and good selectivity, and despite the difficulties of requiring a high vacuum and other engineering challenges, portable and semi-portable mass spectrometers have been developed, by several companies. For example Foster-Monitor Group, of Cheswick Pa., has a mass spectrometer that can collect a sample and identify the component gases based on their molecular masses. Both the portable mass spectrometers and gas chromatographs are capable of identifying an unknown gas. While these devices offer considerable potential, they remain too expensive for routine safety monitoring, and tend to be used for more specialized applications.

Infra-red spectroscopy can also be used to identify a particular gas. Whereas most infrared combustible gas sensors operate at a single wavelength, and thus have difficulty distinguishing between various hydrocarbons, the full infrared spectra of most organic compounds are unique. Thus, if the full spectrum is obtained with an infrared spectrometer, then the spectrum can be compared against a library of infrared spectra. Due to the complexity of the optics, the cost associated with obtaining a full spectrum and the subsequent data analysis increases the cost of this instrument well beyond that normally used for routine safety monitoring.

Sensor arrays have been developed which are capable of identifying a wide range of gases. These sensor arrays effectively have a large number of sensor elements, each with a different response characteristic. The combined pattern of response from a sensor array can indicate the concentration and identify of gaseous species present. However, sensor arrays have two drawbacks. The first drawback is that the pattern recognition requires very complex mathematical analysis, and thus they require a significant computer analysis to achieve useful results. The second and more important drawback is that the present day sensor arrays do not have the reliability necessary for safety applications. It is likely that both of these problems will be overcome in the future, and sensor arrays are now commercially available, for example from Cyrano Sciences Inc, Pasadena, Calif., and are being used for applications such as food quality and wine classification. The operation of these sensor arrays has been described by M. S. Freund and N. S. Lewis in proceedings of the National Academy of Science (1995), 92, 2652–2656 and by N. S. Lewis in U.S. Pat. No. 5,571,401.

As may be seen from the above discussion, there is a need for an economical method that will identify an unknown gas, so that the appropriate calibration and alarm set point values can be selected. The instrument should be economical enough to be incorporated in personnel and fixed-point safety monitoring equipment. Furthermore, the accuracy and precision of the gas concentration measurement should be as good as the present technology, and preferably the instrument should still use the existing sensor technologies, since they are well tested and have a good service record.

Recently, Zdanevitch et al in U.S. Pat. No. 5,709,792 described a method for identifying a combustible gas using a catalytic bead sensor by varying the potential applied to the bead and using the differences in temperature needed to initiate combustion as a means to identify the gas. This method has many advantageous features, but it suffers from the limitation that the temperature of combustion may vary as the sensor catalyst ages or if the sensor is exposed to poisoning or inhibiting compounds. This deleterious effect will be much more pronounced than is normally observed with a conventional sensor operating under diffusion control at a temperature sufficiently high to oxidize all combustible gases, which reach the detector element of a catalytic bead sensor.

SUMMARY OF THE INVENTION

Accordingly, it is an object of the invention to provide a method for identifying an unknown reactive gas which overcomes the disadvantages of prior art methods.

It is a further object of the invention to provide a method for determining concentration of a gas identified by the method of the invention.

It is still a further object of the invention to use the measurements made according to the invention to determine whether the gas detection instrument is operating correctly.

To achieve these and other objects, the invention is directed to a method and apparatus for identifying a gas utilizing a known reactive gas detector including a diffusion barrier inlet which generates an electrical signal upon exposure to the gas. A relative diffusion constant is determined for an unknown reactive gas by comparison of a steady state signal for the unknown gas with the integrated decay signal for the detector exposed to a sealed and predetermined volume of the gas. The relative diffusion coefficient can be compared with the relative diffusion coefficient of a standard gas determined in a similar manner and the resulting actual diffusion coefficient is used to identify the gas.

Once the gas is identified, the concentration can be determined from the value of the steady state signal for the gas.

The invention includes an apparatus for carrying out the method of the invention, including a detector of known type with diffusion barrier inlet, a manifold through which the gas passes and to which the detector is exposed through the diffusion barrier and means for closing the inlet and outlet of the manifold so that the detector is exposed to a fixed volume of gas. The apparatus can include computer means for automating the steps of the invention to any degree desired.

The method of the invention can be used to detect a wide variety of reactive gases. Among the gases which can be detected are combustible gases such as alkanes, alkenes, alkynes, alcohols, ethers, esters and aromatics, and toxic gases such as carbon monoxide, sulfur dioxide, hydrogen sulfide, nitric oxide, nitrogen dioxide and chlorine. The above list is representative only, and should not be considered limiting.

DESCRIPTION OF THE PREFERRED EMBODIMENTS

Figure 1:
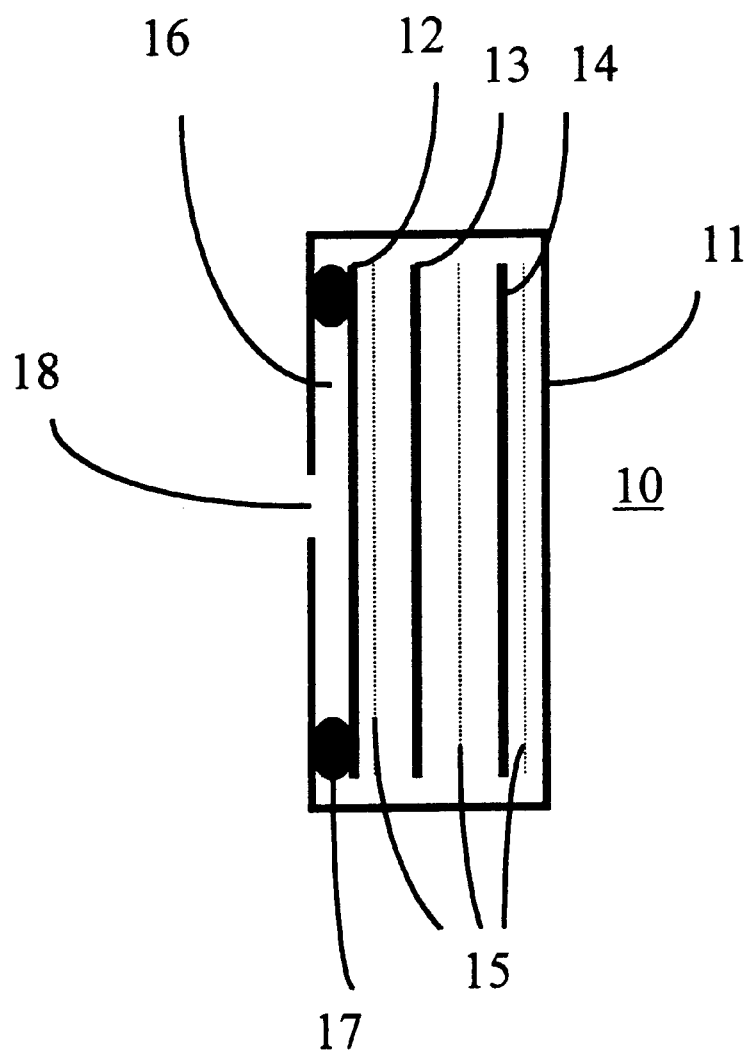
FIG. 1 is a schematic representation of a prior art electrochemical gas sensor.

A typical electrochemical sensor 10 is shown in FIG. 1. The sensor comprises a sensor body 11, containing three electrodes, the working electrode 12, the reference electrode 13 and the counter electrode 14. The three electrodes 12, 13, and 14 are separated by inert media 15, soaked in electrolyte. Typically this inert media 15 is comprised of glass paper, and the electrolyte may be an aqueous or non-aqueous solution of a salt or acid, to provide ionic electrical conductivity between the electrodes 12, 13 and 14. The electrolyte is retained within the sensor 10 and is prevented from entering the gas volume 16 by a compression of an O-ring seal 17, and the electrodes 12, 13 and 14 and the sensor housing 11. The gas to be detected diffuses to the sensor 10 and enters the gas entry hole 18 into a volume 16 within the sensor 10. The gas diffuses through the working electrode membrane 12, which typically comprises a porous membrane with a precious metal (not shown) fixed onto the inner surface of the membrane comprising electrode 12. The magnitude of the steady state response of most amperometric electrochemical gas sensors is limited by the rate at which the gas to be detected can diffuse into the sensor. The sensors are designed to be limited by the rate of gas diffusion by making the gas entry hole 18 small enough that it presents a significant diffusion barrier to the gas. The advantages of making the sensor diffusion limited are that the response is linear with concentration and the sensitivity of the sensor (sensitivity=steady state response to the gas/gas concentration) becomes independent of small variations in electrode potentials, or small losses in electrode catalytic activity.

The operation of this electrochemical sensor has been described for illustrative purposes only and many variations on electrochemical sensor design are known in the prior art. Further details of electrochemical sensor operation and design may be found in the following references: S. C. Chang, J. R. Stetter, C. S. Cha, "Amperometric Gas Sensors", Talanta (1993), 40 (4) 461–477; B. S. Hobbs, A. D. S. Tantram, R. Chan-Henry in "Techniques and Mechanisms in Gas Sensing", Ed. P. T. Moseley, J. O. W. Norris and D. E. Williams, Adam Hilger, Bristol, (1991).

Figure 2:
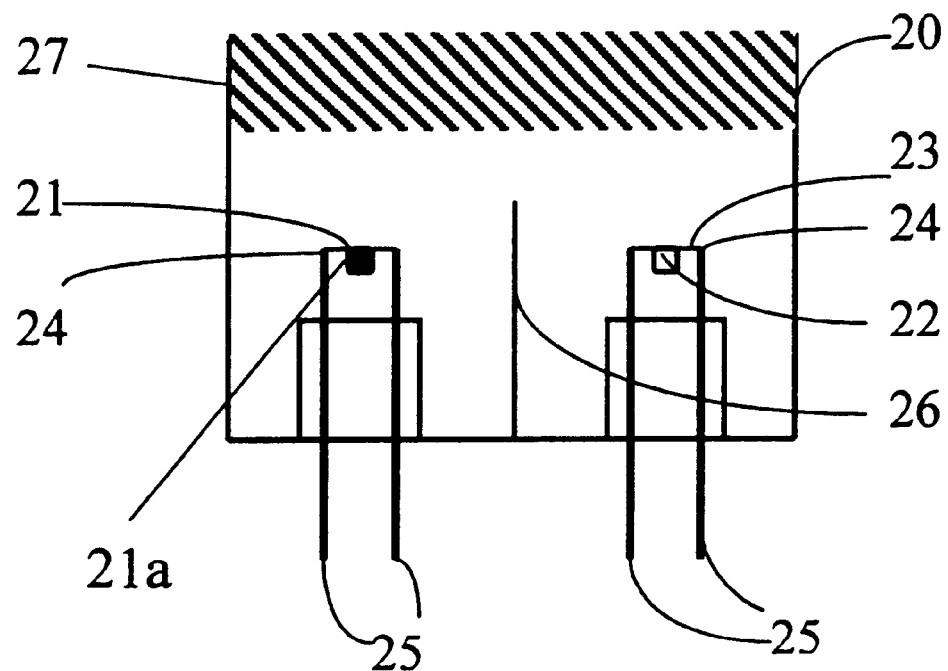
FIG. 2 is a schematic representation of a prior art catalytic bead gas sensor.

A catalytic bead sensor 20, as shown in FIG. 2 usually comprises two beads, a detector 21 and a reference bead 22, the beads comprising a wire coil embedded in alumina or other ceramic. The ends 23 of this wire are attached to posts 24 in such a way as to suspend the beads 21 and 22 between the posts 24. These posts 24 serve the dual role of mechanically supporting the beads 21 and 22, and also providing an electrical connection to external contacts 25. The two beads 21 are 22 are usually separated by a partition 26, which serves to reduce air currents within the sensor 20.

The detector bead 21 additionally has a precious metal catalyst 21a deposited on the surface of the bead 21, whereas the reference bead 22 does not. The beads 21 and 22 are held at a high temperature, typically greater than 500° C., which in combination with the catalyst facilitates the combustion of any combustible gases which reach the detector bead 21. Since the reference bead 22 does not have the catalyst on its surface, no combustion occurs on the reference bead 22. The increase in temperature from the combustion of the combustible gas on the detector bead 21 results in an increase in the resistance of the wire coil inside the bead 21. This small increase in resistance is conveniently detected with a Wheatstone bridge circuit (not shown), and provides the output signal. The gas enters the sensor 20 by diffusing through a sintered metal disk 27, which serves the role of both a diffusion barrier and flame arrestor. Catalytic bead sensors are well known in the prior art, and details may be found in reference texts. (J. G. Firth, "Measurement of Flammable Gases and Vapors" in C. F. Cullis, J. G. Firth (Eds.), "Detection and Measurement of Hazardous Gases", Publ. Heinemann, London, 1981).

In common practice, sensors for gas detection are either operated by exposing the sensor to the ambient atmosphere and thus allowing gas to diffuse into the sensor, or the gas detection instrument may include a pump which draws in the gas from the ambient atmosphere and then passes it over the sensor. The response of the sensor in an aspirated sample gas detection instrument will still be diffusion limited, since the rate at which the gas enters the sensor will still be limited by diffusion.

Figure 3:
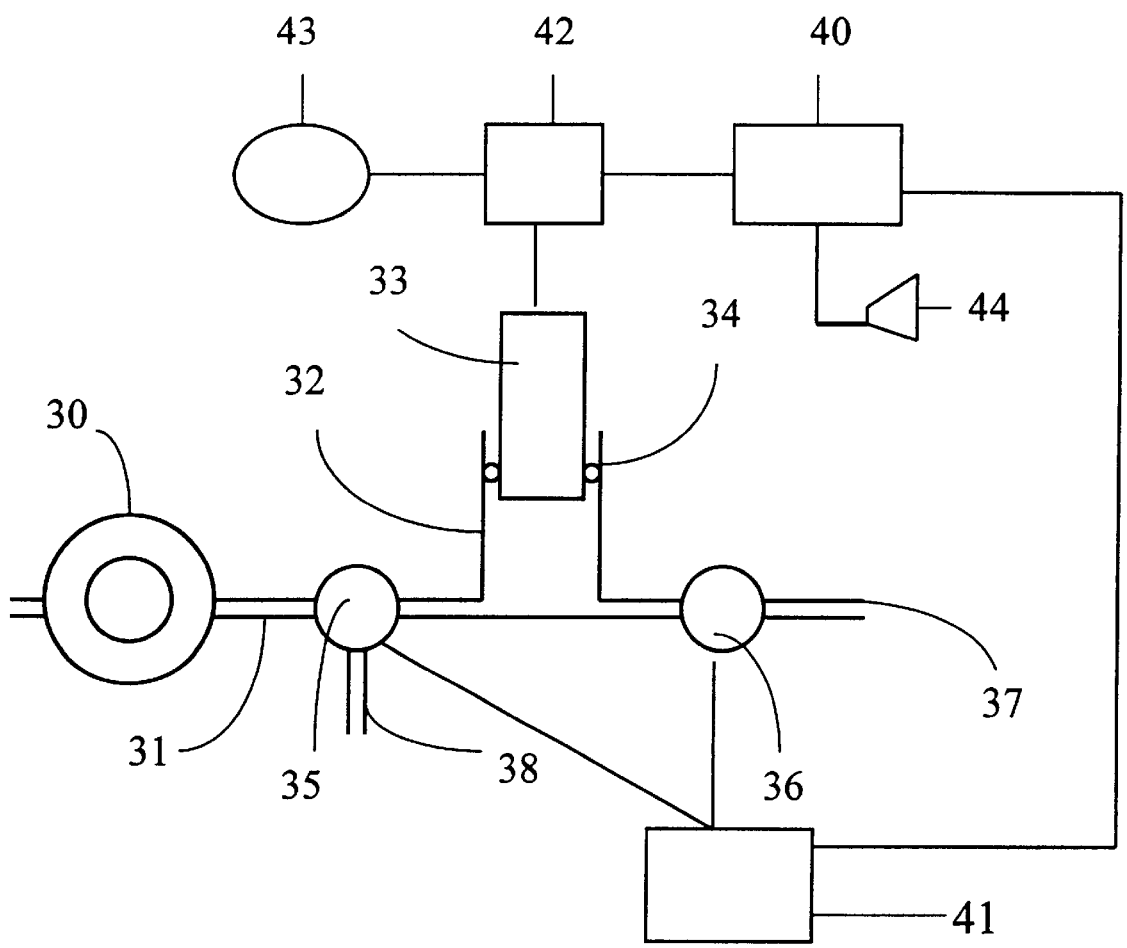
FIG. 3 is a schematic diagram of a gas analysis system according to the invention.

FIG. 3 shows the gas flow system of a first embodiment of a gas detection instrument according to the invention. The gas is drawn in from the ambient atmosphere by the pump 30 and passes through tubing 31 to a two way valve 35. If the valve is activated, then the gas passes through valve 35 into a sensor manifold 32, whereupon the gas diffuses into a sensor 33 of a known type, which gives an output response. The sensor 33 makes an airtight seal with the sensor manifold 32, by means of an O-ring seal 34. The gas passes out of the sensor manifold 32 via valve 36 to an exhaust 37. Valve 36 is open whenever valve 35 is activated and valve 36 is closed whenever valve 35 is not activated. When valve 35 is not activated, the gas from pump 30 is passed to an exhaust 38. The steady state signal from sensor 33 is obtained by having valves 35 and 36 both open.

Consider initially an example in which sensor 33 is an electrochemical gas sensor. For an electrochemical sensor operating under diffusion control, the steady state current $I_{ss}$ (A) is described by Faraday's law $$I_{ss}=nF\phi$$

where n is the number of electrons, F is the Faraday's constant (9.648×10$^4$ C/mol) and $\phi$ is the flux of gas (mol/s) reaching the electrode 12 in FIG. 1.

The flux of gas reaching the electrode 12 is described by Fick's first law of diffusion, $$\phi=-DC\Delta$$

where D is the diffusion coefficient of the gas (cm$^2$/s), $C_o$ is the bulk concentration of the gas (mol/cm$^3$) and $\Delta$ is a parameter which describes the diffusion path of the sensor (cm). The minus sign is usually included in this expression to indicate that the flux of gas is from high concentration to low concentration, but the minus sign will be left out from hereon in for simplicity. These two equations can be combined to give the well know expression for the steady state response $I_{ss}$ of an electrochemical gas sensor.

$$I_{ss}=nFCD\Delta$$

Assume that there is a gas to which the sensor 33 responds in the air drawn into the instrument by pump 30, and the sensor response has reached steady state. If the valves 35 and 36 are then closed, the sensor 33 will consume all of the gas within the volume defined by the two valves 35 and 36, the sensor 33 and the sensor manifold 32. The output current from the sensor 33 will decrease with time, and the total charge Q which passes, is described by the following equation.

$$Q=nFCV$$

Where V (cm$^3$) is the volume of the gas, which is sealed off by the two valves 35 and 36 and the other terms are as defined earlier. The ratio of the steady state current prior to closing the valves 35 and 36 to the charge passed can be calculated as:

$$I_{ss}/Q=(\Delta/V)D$$

Note that the right hand side of this expression is comprised of three constants. The first two, $\Delta$ and V, are constants of the sensor and the gas detection instrument, and independent of the gas. The third constant D, the diffusion coefficient, is a property of the gas being analyzed. Even though the magnitude of response signal depends on the gas concentration, and the number of electrons, these other factors cancel out in calculating $I_{ss}/Q$, leaving D as the only gas dependent variable.

A similar result is obtained if sensor 33 in FIG. 3 is a catalytic bead sensor. The response of a catalytic bead sensor whose response is limited by the rate of gas diffusion can be described by the following equation, which is directly analogous to the respective equation for the electrochemical sensor.

$$S=KHD\Delta C$$

where S is the steady state output signal (mV), C is the bulk concentration, H is a gas specific response constant which varies with the gas, K is a constant of the sensor which is the same for all gases and D and $\Delta$ are the gas diffusion coefficient and a value for the diffusion path of the sensor respectively. If the sensor 33 is placed in the gas flow system shown FIG. 3, the sensor will give a response as a combustible gas is drawn into the instrument by pump 30, provided the valves 35 and 36 are open. If the valves 35 and 36 are closed after the output of sensor 33 has reached steady state S, the output from the sensor 33 will decrease with time. The integrated response of the sensor S over the time it takes for the sensor output to decrease to zero (the response of the sensor in the absence of a combustible gas) is given by the following equation:

$$\Sigma=KHCV$$

If the ratio between the steady state response S and the integrated response $\Sigma$ is calculated, the answer is proportional to the gas diffusion coefficient D.

$$S/\Sigma=(\Delta/V)D$$

Note that as with the electrochemical sensor above, the ratio $\Delta/V$ is dependent on the physical properties of the gas detection instrument and on the sensor and independent of the gas, whereas the diffusion coefficient D is a property of the gas. Note also that the gas concentration and the response constants K and H have also cancelled out of the expression for $S/\Sigma$.

If the sensor is a broad band sensor, which responds to a wide range of different gas types, then this calculation of the diffusion coefficient D can be used to identify the gas. While in principle the diffusion path parameter $\Delta$ and the volume V can be measured, thus allowing the direct calculation of the gas diffusion coefficient, it is more convenient to measure the gas diffusion coefficient relative to a calibration gas. The gas detection instrument would be exposed to gas of known composition and known diffusion coefficient, which would provide a calibration of the system. Then comparison of the ratio of steady state signal to integrated signal passed (S/$\Sigma$ or I/Q) for an unknown gas, can be used to measure the diffusion coefficient of that gas and thus provide identification of the unknown gas.

The diffusion coefficient depends on the molecular weight of both the component gas and the balance gas, and on the molecular size. From a practical standpoint, two similarly sized molecules, for example ethylene ($CH_2$=$CH_2$) and ethane ($CH_3$—$CH_3$) are likely to have similar diffusion coefficients and so it would be more difficult to distinguish between them. Similarly, the two toxic gases nitric oxide (NO) and carbon monoxide (CO) will have similar diffusion coefficients, and so it would be more difficult to distinguish between them using their diffusion coefficients. However, two dissimilar gases, such as methane ($CH_4$) and pentane ($C_5H_{12}$), or carbon monoxide and sulfur dioxide ($SO_2$) will have very different diffusion coefficients, and thus can be more readily distinguished. The ability to distinguish between two different gases will depend on the magnitude of their relative diffusion coefficients and the experimental error in the measurement of the diffusion coefficients.

Once the gas diffusion coefficient has been measured, the gas can be identified by comparison of the diffusion coefficient with values for known gases. Once the gas has been identified, then the correct sensitivity parameters, and alarm threshold limits can be used by the gas detection instrument. Most modern gas detection instruments contain a microprocessor or other controller, and thus it is relatively easy for a gas detection instrument to do the requisite calculations and to access 'look-up' tables within the instrument to compare measured with expected diffusion coefficients and to obtain the sensitivity parameters and the alarm threshold limits.

This method can be used with any type of sensor for which the steady state response is limited by the rate of gas diffusion into the sensor. Furthermore, it is thus possible to identify a gas with a single sensor, and this gas identification may be performed using sensors of well known and well trusted design.

Given that the gas can be identified from the steady state response S and the integrated response $\Sigma$, computer means can be added to the apparatus to automate the identification to the extent desired. As shown in FIG. 3, a central processing unit 40 controls the operation of a device 41 which controls the opening and closing of valves 35 and 36. A device 42 contains the electronic circuitry necessary to operate sensor 33 and to obtain output readings from sensor 33. Such circuits are well known in the art, and include the Wheatstone bridge circuit used in conjunction with a catalytic bead sensor and a potentiostat used in conjunction with an electrochemical sensor. Device 42 may display the readings on a display unit 43, as well as pass the readings on to central processing unit 40. If the unit 40 senses a hazardous condition, an alarm unit 44 is notified.

Typically, central processing unit 40 will store the steady state signal for the background atmosphere or carrier gas. When the presence of a reactive gas is determined, unit 40 will permit a steady state signal S to be established (S is the signal in the presence of the reactive gas minus the background signal in the absence of the reactive gas), then notify device 41 to close valves 35 and 36. Unit 40 then records the decay of the output signal from device 42 and when the output signal reaches the signal for the background, valves 35 and 36 are opened, and monitoring continues. Meanwhile, unit 40 integrates the decay curve to obtain $\Sigma$ and uses $\Sigma$ and S to obtain a diffusion coefficient which can be compared to a list of known coefficients to identify the gas. Once the gas is identified, the response factors and the alarm trigger levels for that gas can be obtained from a list of known values. Using these parameters, unit 40 determines the gas concentration from the steady state signal S, and if concentration exceeds a predetermined level, the alarm unit 44 signals the operator.

Example 1

Figure 4:
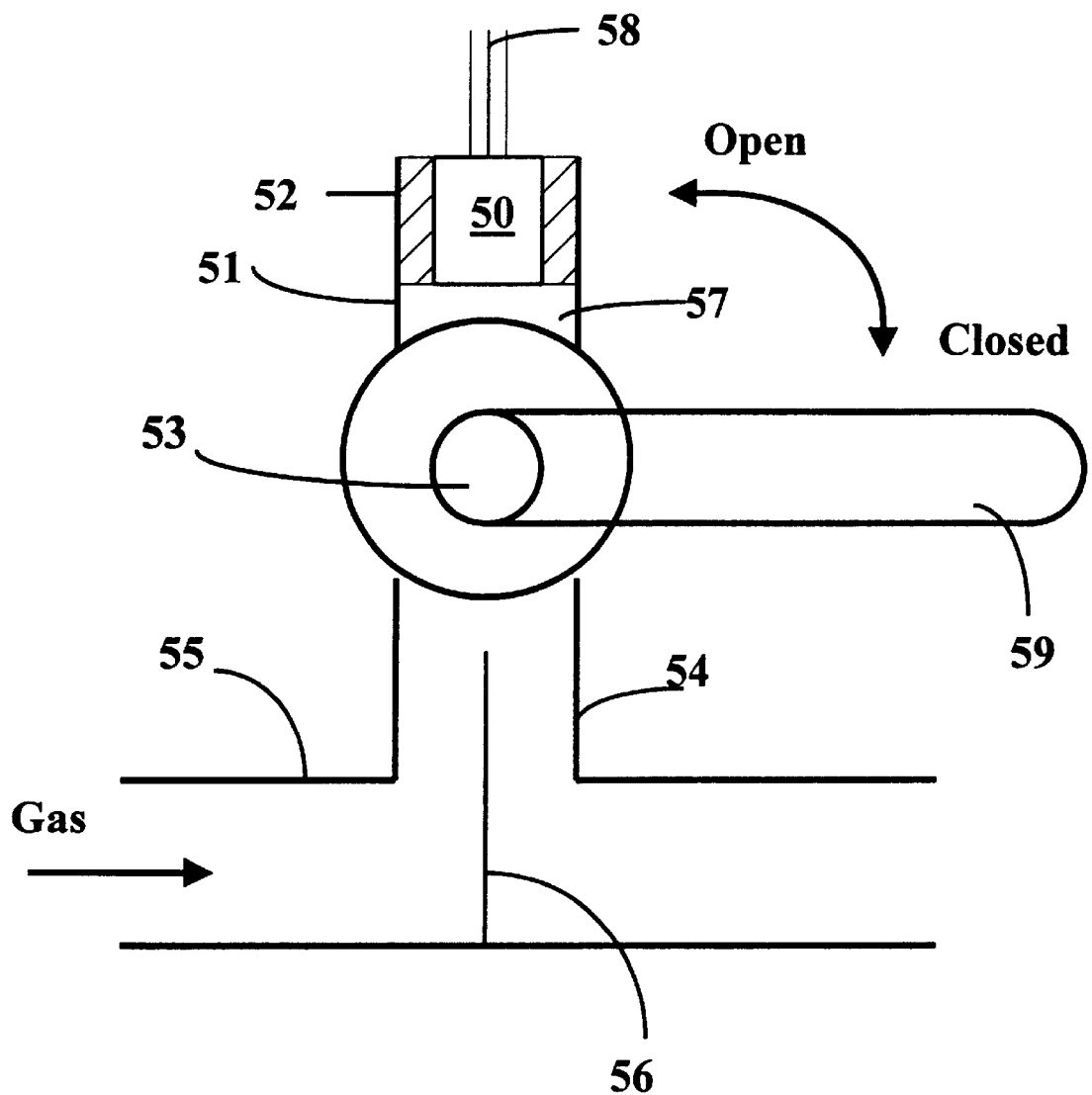
FIG. 4 is a schematic diagram of an alternative gas analysis system according to the invention.

A simple apparatus, shown in FIG. 4, was constructed to demonstrate the practical utility of this invention. A catalytic bead sensor 50 from City Technology, Portsmouth, England, model 4P-100 Cipel, was sealed into a short length of tubing 51 with a gas tight sealant 52 behind a three quarter-inch diameter ball valve 53. The ball valve 53 is connected via a short length of tubing 54 to a T connection to a tube 55 through which the test gas flows. A small baffle 56 was inserted into the tube 54 to promote the flow of gas towards the ball valve 53 and sensor 50. When the ball valve 53 is open, the test gas flows towards the sensor 50. When the ball valve 53 is closed, the flowing gas is prevented from reaching the sensor 50, and the sensor is exposed only to the gas in the sealed volume 57 determined by the sensor 50, sealant 52, tubing 57 and the ball valve 53. The sensor 50 was connected to a Wheatstone bridge detection circuit (not shown) via leads 58, and the output signal was collected on an automated data acquisition system (also not shown). With the ball valve 53 open, the sensor 50 was exposed to the test gas and the output allowed to reach steady state. Once steady state had been reached, the ball valve 53 was closed using handle 59, and the output from the sensor 50 was followed with time as it decayed back to the zero point, i.e. approximately the same signal as was observed with clean air, which was free of combustible gas. The signal from the time when the ball valve 53 was closed to the time when the output signal had decayed to zero was integrated using a spreadsheet program, and the ratio of the steady state signal to the integrated signal (S/$\Sigma$) was calculated.

The apparatus was calibrated using 40% LEL methane in air from a compressed gas cylinder. The steady state signal obtained from sensor 50 in a Wheatstone bridge circuit, when the ball valve 53 was open was 47.7 mV. When the ball valve 53 was closed, the signal decayed to zero. The area under the signal-time graph for the decay was calculated using a Microsoft Excel spreadsheet, and it was found to be 977 mVs. The ratio of the steady state signal to the integrated decay signal was calculated, S/$\Sigma$=0.048 s$^{-1}$.

The equipment was then tested with a test gas A, and the steady state signal for test gas A was 50.2 mV and the integrated decay signal was 312 mVs. Therefore the ratio of the steady state signal to the integrated decay for test gas A was 0.16 s$^{-1}$. The S/$\Sigma$ to ratio for test gas A is 0.16/0.048=3.3 times larger than the S/$\Sigma$ ratio for methane, and thus the diffusion coefficient for test gas A is 3.3 times that of methane.

Diffusion coefficients relative to the calibration gas methane, are shown below. Experimental values of the diffusion coefficient have been tabulated for many gases in the literature, or they can be calculated using standard methods (G. O. Nelson, "Gas Mixtures, Preparation and Control", Lewis Publishers, Boca Raton, Fla., 1992; E. L. Cussler "Diffusion, Mass Transfer in Fluid Systems", Cambridge University Press, Campridge, 1992).

| GAS | Diffusion Coefficient (Relative to Methane) |
| --- | --- |
| Hydrogen | 3.32 |
| Methane | 1.0 (fixed) |
| Butane | 0.49 |
| Pentane | 0.39 |

Thus, by comparison of the experimental ratio of S/Σ for test gas A to the ratio S/Σ for methane, with the relative diffusion coefficients in the table, test gas A is identified as hydrogen.

The experiment was repeated with test gas B. For test gas B, the steady state signal was 17.0 mV and the integrated decay was 633 mVs. The ratio of S/Σ for test gas B was 0.027 s$^{-1}$, which gives a relative diffusion coefficient of 0.55. From the table above, test gas B is identified as butane.

Cross sensitivity is defined as the signal produced per unit of gas concentration of one gas, relative to standard gas. For combustible gases, the concentration is often expressed as a percentage of the lower explosive limit. For the sensor 50 used in this example, the nominal cross sensitivities are as follows, relative to methane (=100%), Hydrogen=100% and Butane=65% (Product Data Handbook, vol. 1, Safety, issue 4.0, January 1997, City Technology Ltd., Portsmouth, United Kingdom).

Having identified test gas A as hydrogen and test gas B as butane, the concentrations can be found from the steady state signal. The steady state output of the sensor exposed to 40% LEL methane in air was 47.7 mV. The steady state signal of the sensor exposed to test gas A was 50.2 mV, and since the cross sensitivity ratio for hydrogen is 100%, the concentration of hydrogen in test gas A is estimated to be 40% LEL: (50.2/(1.0 * 47.7))=42% LEL hydrogen. Similarly, the steady state signal for test gas B was 17.0 mV, and since test gas B was identified as butane, the cross sensitivity ratio (relative to methane) is known to be 65%. Thus, the concentration of butane in test gas B is estimated to be 20% LEL: (17.0/(0.65 * 47.7)=22% LEL butane.

Test gas A was mixture of 50% LEL hydrogen in air produced by blending 100% by volume hydrogen with zero air from compressed gas tanks using an electronic mass flow controller, and test gas B was 0.473% by volume (25% LEL) butane in air from a compressed gas cylinder. The error between the nominal test gas concentration and the measured value are thus 16% for test gas A and 12% for test gas B. This example has thus demonstrated that the method described in this disclosure can be used to both identify an unknown gas, and to estimate the concentration of the gas.

It is well known that gas diffusion coefficients vary with temperature T and usually D is proportional to temperature raised to the power of 3/2 (E. L. Cussler, Diffusion, Mass Transfer in Fluid Systems, Cambridge University Press (1992)), and therefore temperature compensation will be required. Since the response of most sensor types varies with temperature, methods for providing temperature compensation are well known in the prior art pertaining to gas detection instruments.

The gas diffusion coefficient though usually written for a single gas is actually a function of the composition of all of the components of the gas mixture. Therefore, a diffusion coefficient calculated in one gas mixture may differ from that in another gas mixture. In general this issue is not a problem, since most applications for gas detection instruments measure the analyte gas in air. If the air were replaced by another gas, for example helium, then the diffusion coefficients of the gases will change. For example, the diffusion coefficient of an air-oxygen gas mixture is D=0.1775, but an air-helium gas mixture has a diffusion coefficient of 0.6242 cm$^2$/s (E. L. Cussler, Diffusion, Mass Transfer in Fluid Systems, Cambridge University Press (1992)). If this invention is to be used in an application with a balance gas other than air, then the change in the diffusion coefficients can easily be compensated for by calibrating the system with a known gas in a mixture with the same balance gas as the application.

Figure 5:
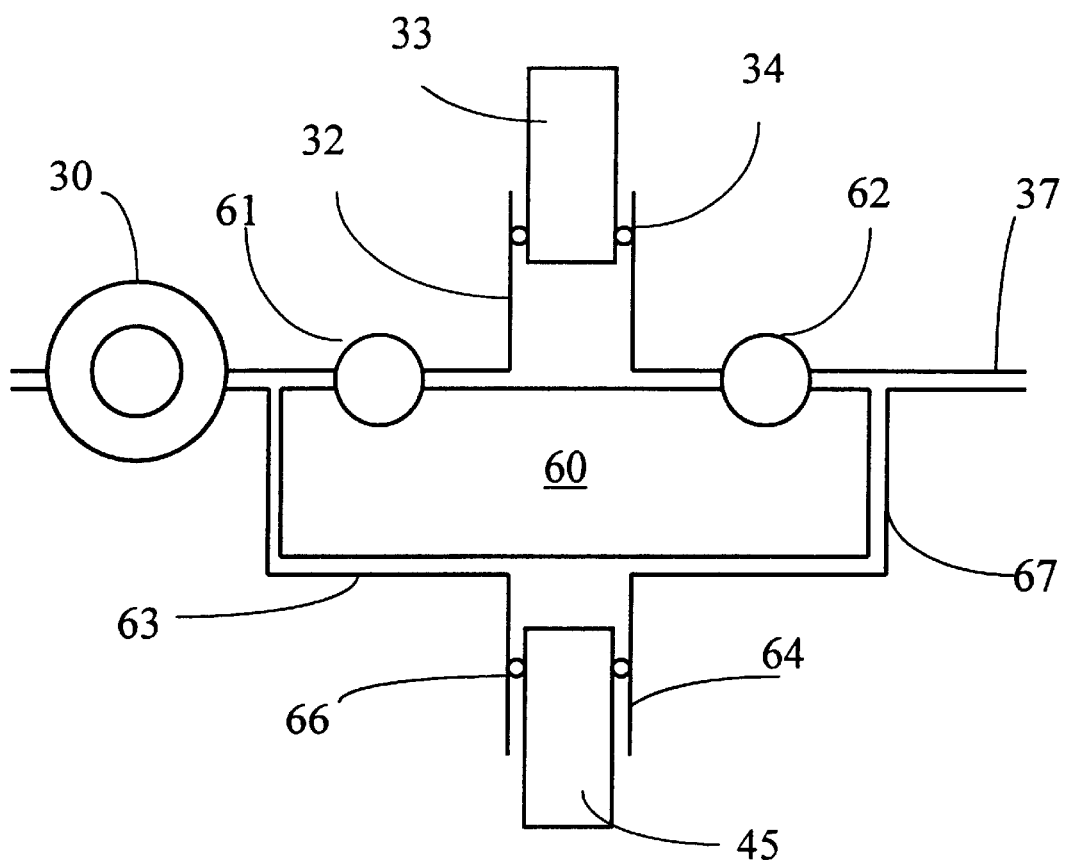
FIG. 5 is a schematic diagram of a further alternative gas analysis system according to the invention.

Obviously, while the valves 35 and 36 in FIG. 3 are closed, the sensor is not able to respond to changes in the gas concentration in the ambient environment. One limitation of the above embodiment of the invention is that the instrument is unable to monitor for changes in the ambient atmosphere during the identification of the gas, since the sensor is exposed to the gas within the sealed compartment. Therefore, another embodiment of this invention uses two sensors, one of which is used to provide continuous monitoring and the other is used to identify the gas. This system 60 is shown in FIG. 5. When valves 61 and 62 are open, gas is pumped by pump 30 into the identification sensor manifold 32, and the identification sensor 33 is exposed to the gas. When valves 61 and 62 are closed, then the sensor 33 consumes all of the gas in the sensor manifold as described above to allow identification of the gas. Gas from pump 30 is also passed through tubing 63 to a second sensor manifold, 64 containing a continuous monitoring sensor 65, which makes a gas tight seal with the manifold by means of O-ring seals 66. After passing through the manifold 64, the gas flows via tubing 67 to the exhaust 37. The gas from pump 30 is always flowing through the tubing 63 and manifold 64, and thus the sensor 65 provides continuous monitoring, even when valves 61 and 62 are closed, thus isolating sensor 33 from changes in the gas composition in the environment.

The time taken to wait for the response to decay to zero once the valves 35 and 36 in FIG. 3, or valves 61 and 62 in FIG. 5 have been closed can take a significant length of time, typically seconds to minutes. The time required will depend on the sensor 33, on the shape and volume of the chamber defined by the valves 35 and 36, or 61 and 62, and on the gas being identified. Furthermore, as the signal approaches zero, the signal to noise ratio decreases and thus it is increasingly difficult to resolve the signal from the background signal, i.e. the signal present without gas.

One way to avoid this problem is to measure the initial decay rate, and then to extrapolate this curve to zero gas signal, by assuming a mathematical function for the signal decay. Provided the gas in the chamber defined by the values 35 and 36, or 61 and 62, can readily diffuse to the sensor 33, then the decay of the output signal may be approximated by an exponential decay. Thus if the initial steady state signal (S or $I_{ss}$) is measured, and the time taken for the signal to decrease to 50% of the initial value after closing the values 35 and 36, or 61 and 62 is measured, then the integrated signal under the curve (Σ or Q) can be calculated.

Using a catalytic bead sensor as an example, and assuming an exponential decay, the output is described by the following equation:

$$S_t = S \cdot \exp(-bt)$$

in which $S_t$ is the output signal at time t, S is the initial steady state signal prior to closing valves 35 and 36, or 61 and 62 and b is a constant. When the output response has fallen to 50% of the steady state value, the expression can be re-written as follows:

$$S_t/S = 0.5 = \exp(-bt_{50})$$

in which $t_{50}$ is the time taken for the signal to decrease to 50% of the initial value from the initial time (t=0) when the valves 35 and 36, or 61 and 62 were closed. Rearranging this equation for b gives the following result:

$$b = 0.693/t_{50}$$

Integration of the function $S_t = S \cdot \exp(-bt)$ with respect to time, gives the cumulative signal $\Sigma$:

$$\Sigma = [-S/b(\exp(-bt))]$$

Evaluating this function from the times that the valves 35 and 36, or 61 and 62 were closed (t=0) to long times (t=>∞), gives the result $$\Sigma = S/b$$

Since the steady state current S is known, and the constant b can be measured, the integrated response can be found more quickly than having to wait for the response to decay to zero.

This method of extrapolating the time taken for an exponential decay is well known in the prior art, and it is included here to illustrate the principle. Clearly, many other methods of extrapolating the decay are possible, and are well known to those experienced in the art. For example, Tantram et al in U.S. Pat. No. 4,829,809 disclose a method for measuring the concentration of a gas by exposing an electrochemical sensor to a known volume of the gas to be measured. The output signal from the sensor decays as the gas is consumed, and by measuring the total charged passed, and knowing how many electrons are passed for the oxidation or reduction of the gas, they can use Faraday's law to calculate the concentration of the gas.

$$C = Q/nFV$$

Rather than wait for the sensor response to decay all the way to zero, Tantram et al propose a method for speeding up the measurement, by assuming an exponential decay, and extrapolating to zero current. The apparatus described by Tantram et al is similar to that described in FIG. 3 of this application. Thus, once the gas had been identified using the method described in this disclosure, it is possible to measure the concentration of the gas using the method of Tantram et al. For a catalytic bead sensor, a similar relationship exists, and thus the concentration of a combustible gas sensor can also be found.

$$C = \Sigma/KHV$$

However, whereas Faraday's constant is a physical constant available in any physical chemistry data book, the constant K for the catalytic bead sensor will vary from sensor to sensor, and H is a gas specific constant. Once the gas has been identified, then the gas specific constant H can be used, if previously determined. For most combustible gases, H is approximately equal to one, if the response is calculated in terms of the LEL. The constant K is most conveniently determined by calibrating the gas detection instrument with a gas of known identity and of known gas concentration.

In a further embodiment of this invention, if the identity of the test gas is known, and the sensor response is limited by diffusion, then if the calculated gas diffusion coefficient is close to the expected value, then the sensor is deemed to be operating under diffusion control. However, if the measured diffusion coefficient differs greatly from the expected value of the diffusion coefficient, then there is a problem with either the instrument, the gas delivery system (e.g. blocked tubing), or with the sensor. Thus this method can also be used to ascertain the functional status of the sensor and instrument. While this invention has been described for electrochemical and catalytic bead sensors, it is readily apparent that the same invention may be applied to any kind of sensor whose response is limited by the diffusion rate of the analyte species. Moreover, it will be evident to those skilled in the art that numerous variations of the details may be made without departing from the invention as defined in the

What is claimed is:

1. Apparatus for identifying and quantifying a reactive gas in a carrier gas, comprising:

a manifold of predetermined volume having an inlet and outlet;

an inlet valve in the manifold inlet;

an outlet valve in the manifold outlet;

a gas detector in communication with the manifold;

a diffusion barrier disposed between the manifold and the gas detector for limiting diffusion of gas from the manifold into the gas detector;

means for opening and closing the inlet and outlet valves;

means for detecting an output signal from the gas detector;

means for determining a coefficient of diffusion for the reactive gas from the output signal; and means for identifying and quantifying the reactive gas from the determined coefficient of diffusion.

2. Apparatus according to claim 1, additionally comprising a gas pump having an outlet connected to the inlet valve.

3. Apparatus according to claim 1, additionally comprising:

a further manifold of predetermined volume having an inlet and outlet;

a further gas detector in communication with the further manifold; and a further diffusion barrier disposed between the further manifold and the further gas detector for limiting diffusion of gas from the further manifold into the further gas detector;

said further manifold being constructed and arranged to receive a flow of atmosphere when said inlet and outlet valves are closed.

4. The apparatus of claim 1, additionally comprising:

computer means for controlling the means for opening and closing the inlet and outlet valves;

computer means for memorizing steady state values for the output signal;

computer means for generating and integrating an output signal vs. time curve for a time during which the inlet and outlet valves are closed; and computer means for obtaining a diffusion constant for the reactive gas from a steady state output value for the reactive gas and the integrated output signal.

5. The apparatus of claim 4, additionally comprising computer means for comparing the obtained diffusion constant to known diffusion constants and identifying the reactive gas from the comparison.

6. The apparatus of claim 5, additionally comprising alarm means operable when the output signal exceeds a predetermined value.

7. The apparatus of claim 1, additionally comprising a display means for the output signal.

8. The apparatus of claim 1, wherein the gas detector is a catalytic bead detector.

9. The apparatus of claim 1, wherein the gas detector is an electrochemical detector.

10. The apparatus of claim 1, wherein the diffusion barrier is a membrane or a hole.

11. Apparatus for determining a coefficient of diffusion for an unknown reactive gas in a carrier gas, to enable identifying and quantifying the unknown reactive gas, comprising:

- a manifold of predetermined volume having an inlet and outlet;
- an inlet valve in the manifold inlet;
- an outlet valve in the manifold outlet;
- a gas detector in communication with the manifold;
- a diffusion barrier disposed between the manifold and the gas detector for limiting diffusion of gas from the manifold into the gas detector;
- computer means for opening and closing the inlet and outlet valves;
- means for detecting an output signal from the gas detector; and
- means for determining a coefficient of diffusion for the reactive gas from the output signal, said means comprising computer means for memorizing steady state values for the output signal, computer means for generating and integrating an output signal vs. time curve for a time during which the inlet and outlet valves are closed and computer means for obtaining a diffusion constant for the reactive gas from a steady state output value for the reactive gas and the integrated output signal.

12. The apparatus of claim 11, additionally comprising computer means for comparing the obtained diffusion constant to known diffusion constants and identifying the reactive gas from the comparison.

13. The apparatus of claim 11, additionally comprising alarm means operable when the output signal exceeds a predetermined value.

* * * * *